United States Patent [19]

Goodrich, Jr. et al.

[11] Patent Number: 4,874,690
[45] Date of Patent: Oct. 17, 1989

[54] LYOPHILIZATION OF RED BLOOD CELLS

[75] Inventors: Raymond P. Goodrich, Jr.; Christine M. Williams, both of Pasadena, Calif.; Robert S. Franco; Murray Weiner, both of Cincinnati, Ohio

[73] Assignee: Cryopharm Corporation, Pasadena, Calif.

[21] Appl. No.: 237,588

[22] Filed: Aug. 26, 1988

[51] Int. Cl.$^4$ .............................................. A01N 1/02
[52] U.S. Cl. ........................................ 435/2; 424/101
[58] Field of Search ............................. 435/2; 424/101

[56] References Cited

U.S. PATENT DOCUMENTS

| | | |
|---|---|---|
| 3,347,745 | 10/1967 | Rinfret . |
| 4,061,537 | 12/1977 | Seller . |
| 4,267,269 | 5/1981 | Grode . |
| 4,320,111 | 3/1982 | Hirsch . |
| 4,476,221 | 10/1984 | Kane et al. ............................ 435/2 |
| 4,585,735 | 4/1986 | Meryman . |

FOREIGN PATENT DOCUMENTS

| | | |
|---|---|---|
| 57-7419 | 6/1980 | Japan . |
| 07419 | 1/1982 | Japan . |
| 2163029 | 7/1975 | U.S.S.R. . |
| 197809 | 9/1977 | U.S.S.R. . |
| 686732 | 9/1979 | U.S.S.R. . |
| 2483754 | 9/1979 | U.S.S.R. . |
| 2923438 | 4/1980 | U.S.S.R. . |
| 959786 | 9/1982 | U.S.S.R. . |
| 1144215 | 3/1969 | United Kingdom . |

OTHER PUBLICATIONS

Terekhov et al.—Chem. Abst. vol. 87 (1977) p. 36568b.

*Primary Examiner*—Sam Rosen
*Attorney, Agent, or Firm*—Flehr, Hohbach, Test, Albritton & Herbert

[57] ABSTRACT

A process and medium are disclosed for the lyophilization of red blood cells which comprises the use of solutions including monosaccharide hexoses and pentoses, biocompatible polymers and polyanions to permit the reconstitution of viable red blood cells.

9 Claims, No Drawings

LYOPHILIZATION OF RED BLOOD CELLS

FIELD OF THE INVENTION

This invention relates to the general field of biochemistry and medical sciences, and specifically to processes for the preservation, storage and reconstitution of red blood cells.

BACKGROUND AND SUMMARY OF THE INVENTION

Blood is a major tissue of the human body, and has as a predominant role the delivery of oxygen from the lungs to peripheral tissues. This role is carried out by erythrocytes, i.e., red blood cells (RBC). The oxygen is furnished to the peripheral cells from the lungs by an exchange-diffusion system brought about by a red, iron-containing protein called hemoglobin. When hemoglobin combines with oxygen, oxyhemoglobin is formed an when oxygen is given up to the tissues, the oxyhemoglobin is reduced to deoxyhemoglobin.

The red cell membrane is composed of two major structural units, the membrane bilayer and a cytoskeleton. A lipid bilayer and integral membrane proteins form the membrane bilayer, which has little structural strength and fragments readily by vesiculation. The other major component, the membrane skeleton, stabilizes the membrane bilayer and provides resistance to deformation. The cytoskeleton is linked to the bilayer in the erythrocyte membrane, possibly by lipid-protein as well as protein-protein associations. The hemoglobin, and other RBC components, are contained within the red cell membrane.

In adults, bone marrow is active in the formation of new red blood cells. Once erythrocytes enter the blood, these cells have an average lifetime of about 120 days. In an average person, about 0.83% of the erythrocytes are destroyed each day by phagocytosis, hemolysis or mechanical damage in the body, and the depleted cells are renewed from the bone marrow.

A wide variety of injuries and medical procedures require the transfusion of whole blood or a variety of blood components. Every patient does not require whole blood and, in fact, the presence of all of the blood components can cause medical problems. Separate blood fractions can be stored under those special conditions best suited to assure their biological activity at the time of transfusion. For example, when donor blood is received at a processing center, erythrocytes are separated and stored by various methods. Such cells are storable in citrate-phosphate-dextrose at 4° C. for up to five weeks, generally as a unit of packed erythrocytes having a volume of from 200 to 300 ml and a hematocrit value (expressed as corpuscular volume percent) of 70 to 90. Erythrocytes may also be treated with glycerol and then frozen at from $-30°$ to $-196°$ C. and stored for up to seven years in a glycerol solution, but must be kept frozen at low temperatures in order to survive sufficiently for transfusion. Both these methods require careful maintenance of storage temperature to avoid disruption of the desired biological activity of the erythrocytes, and provide a twenty-four hour survival time for at least 70% of the transfused cells, which is considered to be an acceptable level for use in transfusion practice in accordance with the American Association of Blood Bank standards.

It has thus been a desideratum to obtain a method for the storage of red blood cells which is not dependent on the maintenance of specific storage temperatures or other storage conditions. Such a method would facilitate the availability of erythrocytes for medical purposes.

One such desired method has been the lyophilization (freeze-drying) of red blood cells, since such cells could be stored at room temperature for an extended period of time and easily reconstituted for use in mammals. However, prior to our invention, it has been impossible to freeze dry erythrocytes in a manner which permits the reconstitution of the cells to form erythrocytes with an intact cytoskeleton and biologically-active hemoglobin, i.e., viable red blood cells. When RBCs have been lyophilized according to previous methods, for example in either an aqueous or phosphate-buffered saline (PBS) solution, the reconstituted cells are damaged to the extent that the cells are not capable of metabolizing, and the cell hemoglobin cannot carry oxygen. Glutaraldehyde-fixed erythrocytes, which have been lyophilized and reconstituted, have found use primarily in agglutination assays.

The process of the present invention allows for the lyophilization of erythrocytes under conditions which maintain structure of the cell and the biological activity of the hemoglobin, and which permits the reconstitution of the lyophilized red blood cells to allow use on a therapeutic level. Briefly, the process comprises immersing a plurality of erythrocytes in a physiologic buffered aqueous solution containing a carbohydrate, a biologically compatible polymer, and a biologically compatible compound having a plurality of anionic groups, that is, a polyanion. This immersion is followed by freezing the solution, and drying the frozen solution to yield freeze-dried erythrocytes which, when reconstituted, produce a significant percentage of viable red blood cells.

The carbohydrate is biologically compatible with the RBCs, that is, non-disruptive to the cells, and one which permeates, or is capable of permeating, the membrane of the erythrocytes. The carbohydrate may be selected from the group consisting of monosaccharides, since disaccharides do not appear to permeate the membrane to any significant extent. Monosaccharide pentoses and hexoses are preferred as is a concentration of from about 7.0 to 37.5%, preferably about 23%. Xylose, glucose, ribose, mannose and fructose are employed to particular advantage.

The polymer may be present in the solution in concentrations of from 0.7% up to saturation, and has a molecular weight in the range of from about 5K to about 360K. Preferably, the polymer has a molecular weight in the range of from about 5K to about 80K, most preferably from about 5K to 50K, and is present in a concentration of from about 3.6% up to the limit of solubility of the polymer in the solution. Polymers selected from the group consisting of polyvinylpyrrolidone (PVP) and polyvinylpyrrolidone derivatives, and dextran and dextran derivatives provide significant advantages. Amino acid based polymers (i.e., proteins) or hydroxyethyl starch may also be employed.

The polyanion can be any which is non-disruptive to the cell membrane of the erythrocytes, and polyanions having multiple phosphate, sulfate or carboxylate groups are preferred and may be present in amounts of from 0.01 weight percent up to saturation in the solution although a minimum concentration of from about 0.1 up to about 1.0% is advantageous. More preferably, the polyanion is a compound having anionic groups which are phosphate, sulfate or carboxylate groups. Specifically, polyanions selected from the group consisting of pyrophosphate, tripolyphosphate, phosphorylated inositols (including triphosphoinositide and inositol hexaphosphate), 2,3 diphosphoglycerate, adenosine triphosphate, and heparin may be employed to significant advantage.

Additional advantages accrue from the use of a polymeric compound, such as those mentioned above, which bear a plurality of the above described anionic groups in place of both the polymer and polyanion. For example, use of the dextran derivative phosphorylated dextran is advantageous in that it provides the advantages of the polymer and also serves as a polyanion in the solution. Compounds such as phosphorylated dextran thus function as the equivalent of a polymer and a polyanion.

As is shown by the data set forth below, the described solutions provide media which permit red blood cells to be subjected to the stresses of freezing, sublimation and reconstitution and to form freeze-dried red blood cells which may be reconstituted to yield cells which are capable of functioning as erythrocytes in mammals.

Unless indicated otherwise by the terminology or the context, all percentages set forth herein are expressed as weight percentages (i.e. weight of the solute versus the total weight of the solution).

DESCRIPTION OF THE PREFERRED EMBODIMENT

As noted above, the process of the invention provides a medium for the lyophilization and reconstitution of intact and biologically-active erythrocytes. While the media of the invention are novel it will be understood that apparatus and related techniques are known by those of skill in the art for the lyophilization of various materials, and cells in particular, and only the specific temperatures and apparatus employed in the examples are described herein. From this description, one of ordinary skill in the art will be capable of employing the media of the invention in a process for the freeze-drying and reconstitution of intact, viable red blood cells.

The term lyophilization is broadly defined as freezing a substance and then reducing the concentration of one of the solutes, namely water, by sublimation and desorption, to levels which will no longer support biological or chemical reactions. Usually, the drying step is accomplished in a high vacuum. However, with respect to the storage of cells and particularly erythrocytes, the extent of drying (the amount of residual moisture) is of critical importance in the ability of cells to withstand long-term storage at room temperature. In the method of the invention, cells may be lyophilized to a residual water content of less than 10%, preferably less than 5%, and most preferably to a water content of less than 3%.

EXAMPLE ONE

Packed red blood cells of variable blood type were obtained from a hospital blood donor center or drawn from healthy volunteers using heparin as an anticoagulant.

Repeated samples of these blood cells were washed with a phosphate buffered saline solution (10 mM mono- and di-basic sodium phosphate, 150 mM sodium chloride, 5 mM dextrose, and 10 mM adenosine at pH 7.2) three times with centrifugation at 14,000 rpm for 6 to 10 seconds to separate plasma and/or other cell types from the red blood cells.

Samples of these packed red blood cells were then suspended in a lyophilizing buffer containing a 21.7 to 26.3% glucose, 18.1% 10K or 12.8% 24K polyvinylpyrrolidone, and 2.3% inositol hexaphosphate (IHP) in either PBS or deionized water at pH 7.2. No significant difference in results was noted when deionized water was substituted for PBS.

The suspension was then transferred to a flask which was subsequently immersed in liquid nitrogen ($-196°$ C.) until the sample was frozen. The flask was rotated evenly in the liquid nitrogen to assure even dispersion of solution on the walls of the flask.

The frozen sample was transferred to a bench top lyophilizer (Labconco model 4.5) operating at less than 100 micron of mercury vacuum with an inner chamber temperature of $-56°$ C. Samples were allowed to dry thoroughly (6–24 hours) until crystalline in appearance and brittle to touch and the flask was allowed to return to room temperature.

The samples were rehydrated at 37° C. using a solution containing 25.5% sucrose in a phosphate buffered saline solution. A volume of the rehydrating solution was added equivalent to the initial volume of the sample prior to drying.

The samples were centrifuged at 14,000 rpm for about 20 seconds in an Eppendorf microcentrifuge, or until pelleted, to pellet the rehydrated red blood cells in suspension.

Results were assessed as follows:

TABLE I

| Polymer | Polyanion | Cell Recovery | Hb Recovery |
|---|---|---|---|
| 18.1% 10K PVP | 2.3% IHP | 52.4 ± 9.7 | 39.2 ± 8.6 |
| 18.1% 10K PVP | — | 50.4 ± 10.8 | 38.3 ± 10.3 |
| 12.8% 24K PVP | 2.3% IHP | 62.0 ± 10.2 | 61.7 ± 5.1 |
| 12.8% 24K PVP | 0.7% Pyro-phosphate | 64.6 ± 10.4 | 66.9 ± 4.9 |
| 12.8% 24K PVP | — | 56.2 ± 7.7 | 57.5 ± 3.8 |

Red blood cells lyophilized in PBS alone resulted in 0% cell recovery and 0% hemoglobin recovery.

EXAMPLE TWO

The procedures described in Example One were repeated substituting other carbohydrates for glucose in the lyophilizing buffer. Except as indicated, all other components and conditions were identical to those listed in Example Two. The results are summarized as follows:

TABLE II

| Polymer | Carbohydrate | % Hb Recovery w/o Polyanion | % Hb Recovery w/Polyanion |
|---|---|---|---|
| 18.1% 10K PVP | Mannose | 30.6 | 49.6* |
| 18.1% 10K PVP | Xylose | 32.3 | 55.0* |
| 12.8% 24K PVP | Mannose | 55.9 | 70.1** |
| 12.8% 24K PVP | Xylose | 57.2 | 62.4** |

*with 2.3% IHP.
**with 0.7% Pyrophosphate.

Trehalose and sucrose in the lyophilizing solution showed marginal cell recovery, but no hemoglobin recovery. Maltose showed no cell or hemoglobin recovery.

EXAMPLE THREE

The experiment described in Example One was repeated substituting polyvinylpyrrolidone of different molecular weights and concentrations for those used in the lyophilizing buffer of the previously described Example. Except as indicated, all other conditions were repeated as described in Example One. The results are summarized as follows:

TABLE III(a)

| MW | Conc. (%) | % Cell Recovery | % Hb Recovery |
|---|---|---|---|
| 40K | 6.8 | 48.4 | 43.0 |
| | 18.1 | 44.8 | 42.2 |
| | 6.8 | 42.3 | 38.4 |
| | 18.1 | 49.7 | 53.9 |
| 360K | 3.5 | 40.3 | 35.1 |

The use of 1.4% 360K PVP in this Example resulted in totally lysed cells and no hemoglobin recovery.

TABLE III(b)

| MW | Conc. (%) | % Hb Recovery w/o Polyanion | % Hb Recovery w/o 7% Pyrophosphate |
|---|---|---|---|
| 10K PVP | 3.5 | 13.6 | 19.2 |
| | 6.8 | 15.0 | 32.7 |
| | 12.8 | 30.1 ± 4.1 | 26.5 |
| | 18.1 | 38.3 ± 10.3 | 47.7 |
| 24K PVP | 3.5 | 24.7 | 36.5 |
| | 6.8 | 52.9 | 41.8 |
| | 12.8 | 52.7 ± 6.3 | 66.9 ± 4.9 |
| | 18.1 | 52.2 ± 6.9 | 72.1 |

EXAMPLE FOUR

The experiment described in Example One was repeated using polymers other than polyvinylpyrrolidone in the lyophilizing buffer. The results are summarized as follows:

TABLE IV

| | MW | Conc. (%) | % Cell Recovery | % Hb Recovery |
|---|---|---|---|---|
| POLYMER | | | | |
| Dextran | 10K | 18.1 | 43.9 | 20.3 |
| | 40K | 18.1 | 39.3 | 21.9 |
| | 80K | 6.8 | 47.6 | 11.1 |
| Ficoll | 400K | 3.5 | 46.2 | 18.7 |
| Dextran Phosphate | 40K | 6.8* | 56.8 | 37.0 |
| PROTEINS | | | | |
| Albumin | | 6.8 | 60.4 | 29.6 |
| Fish Gelatin | | 6.8 | 39.3 | 28.4 |

*From NMR, this sample consisted of 99% dextran with about 1% of the glucose residues in the polymer phophorylated.

EXAMPLE FIVE

The experiment described in Example One was repeated using varying concentrations of inositol hexaphosphate and pyrophosphate with 18.1% 10K PVP. All other conditions were identical to those described in Example One. The results are summarized as follows:

TABLE V

| Polyanion | Conc. (%) | % Hb Recovery | % Cell Recovery |
|---|---|---|---|
| Pyrophosphate | 0.09 | 37.6 | 56.5 |
| | 0.22 | 39.4 | 57.3 |
| | 0.45 | 62.3 | 63.0 |
| | 0.90 | 61.0 | 64.4 |
| | 1.8 | 54.4 | 56.2 |
| | 4.5 | 24.0 | 33.7 |
| IHP | 0.009 | 30.2 | 67.3 |
| | 0.09 | 42.6 ± 3.7 | 50.3 ± 6.1 |
| | 0.22 | 50.3 ± 6.9 | 55.4 ± 4.0 |
| | 0.45 | 52.4 ± 12.8 | 52.7 ± 12.8 |
| | 0.9 | 58.3 ± 16.4 | 51.9 ± 2.7 |

TABLE V-continued

| Polyanion | Conc. (%) | % Hb Recovery | % Cell Recovery |
|---|---|---|---|
| | 1.8 | 45.0 ± 5.4 | 55.5 ± 3.9 |
| | 4.5 | 34.7 ± 2.7 | 52.5 ± 1.0 |

EXAMPLE SIX

The experiment described in Example One was repeated using polyanions other than inositol hexaphosphate or pyrophosphate in the lyophilizing buffer. All other conditions were the same as those described in Example One. The results are described as follows:

TABLE VI

| Polyanion | % Conc. | % Hb Recovery | % Cell Recovery |
|---|---|---|---|
| Tripolyphosphate | 1.0 | 60.7 | 64.6 |
| Trimetaphosphate | 0.8 | 10.4 | 26.5 |
| ATP | 0.5 | 62.7 | 70.9 |
| 2,3 DPG | 0.7 | 64.1 | 59.4 |

ATP refers to Adenosine 5-triphosphate and 2,3 DPG refers to 2,3 Diphosphoglycerate.

From the foregoing description, one skilled in the art can readily ascertain that essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A process for the lyophilization of erythrocytes, comprising immersing a plurality of erythrocytes in a buffered solution which includes:
   a monosaccharide which is present in the solution in a concentration of from about 7.0 to 37.5%;
   a polymer having a molecular weight of from about 5K to about 80K which is present in a concentration of from about 0.7% up to saturation in the solution;
   a polyanion which is present in a concentration of from 0.01 weight percent up to saturation in the solution;
   freezing the solution; and
   drying the erythrocytes by sublimation of the water.

2. The process of claim 1 wherein the monosaccharide is selected from the group consisting of pentoses and hexoses.

3. The process of claim 1 wherein the monosaccharide is selected from the group consisting of xylose, glucose, ribose, mannose and fructose.

4. The process of claim 1, 2 or 3 wherein the polymer is selected from the group consisting of polyvinylpyrrolidone, dextran and gelatin.

5. The process of claim 1, 2 or 3 wherein the polyanion is a compound having anionic groups which are phosphate, sulfate or carboxylate groups.

6. The process of claim 4 wherein the polyanion is a compound having anionic groups which are phosphate, sulfate or carboxylate groups.

7. The process of claim 1, 2 or 3 wherein the polyanion is selected from the group consisting of pyrophosphate, tripolyphosphate, phosphorylated inositols, 2,3 diphosphoglycerate, adenosine triphosphate, phosphorylated dextran, heparin and polycarboxylic acids.

8. The process of claim 4 wherein the polyanion is selected from the group consisting of pyrophosphate, tripolyphosphate, phosphorylated inositols, 2,3 diphosphoglycerate, adenosine triphosphate, phosphorylated dextran, heparin and polycarboxylic acids.

9. A process for the lyophilization of erythrocytes having a cell membrane, comprising:
   immersing a plurality of erythrocytes in a buffered solution which includes
   (a) monosaccharide selected from the group consisting of xylose, glucose, ribose, mannose and fructose, the monosaccharide being present in the solution in a concentration of from about 7.0 to 37.5%;
   (b) a biocompatible polyanion selected from the group consisting of pyrophosphate, tripolyphosphate, phosphorylated inositols, 2,3 diphosphoglycerate, adenosine triphosphate, phosphorylated dextran, heparin and polycarboxylic acids, the polyanion being present in the solution in a concentration of at least 0.01 weight percent;
   (c) a polymer selected from the group consisting of polyvinylpyrrolidone and dextran, the polymer being present in the solution in a concentration of at least 0.7%;
   freezing the solution, and
   drying the erythrocytes by sublimation of the water.

* * * * *

UNITED STATES PATENT AND TRADEMARK OFFICE
CERTIFICATE OF CORRECTION

PATENT NO. : 4,874,690

DATED : October 17, 1989

INVENTOR(S) : Goodrich, Jr., et al.

It is certified that error appears in the above-identified patent and that said Letters Patent is hereby corrected as shown below:

Col. 5, line 19 (Table III(b)), please delete "w/o 7%" and substitute therefor --w/ 0.7%--; and Col. 5, line 48 (Table IV), please delete "phophorylated" and substitute therefor --phosphorylated--.

Signed and Sealed this

Twelfth Day of November, 1991

Attest:

HARRY F. MANBECK, JR.

Attesting Officer

Commissioner of Patents and Trademarks